United States Patent [19]
Ayers et al.

[11] Patent Number: 5,813,999
[45] Date of Patent: Sep. 29, 1998

[54] IMPLANTABLE ATRIAL DEFIBRILLATOR PROVIDING REDUCED CARDIOVERSION DISCOMFORT

[75] Inventors: Gregory M. Ayers, Duvall; Darrell O. Wagner, Gold Bar, both of Wash.

[73] Assignee: InControl, Inc., Redmond, Wash.

[21] Appl. No.: 576,671

[22] Filed: Dec. 21, 1995

[51] Int. Cl.⁶ ........................................ A61N 1/00
[52] U.S. Cl. ........................ 604/890.1; 128/702
[58] Field of Search ............... 607/6, 7; 128/419, 128/702, 642, 705, 696, 697; 604/890.1

[56] References Cited

U.S. PATENT DOCUMENTS

| | | | |
|---|---|---|---|
| 5,184,616 | 2/1993 | Weiss ................................. | 128/419 |
| 5,251,624 | 10/1993 | Bocek et al. ..................... | 607/6 |
| 5,489,293 | 2/1996 | Pless et al. ....................... | 607/7 |
| 5,605,159 | 2/1997 | Smith et al. ..................... | 128/702 |

*Primary Examiner*—Michael Buiz
*Assistant Examiner*—Manuel Mendez
*Attorney, Agent, or Firm*—Richard O. Gray, Jr.

[57] ABSTRACT

An implantable atrial cardiovertor applies cardioverting electrical energy to atria of a heart with reduced discomfort to a patient. The cardiovertor includes a storage capacitor having a capacitance and a discharge control for controlling discharge of the storage capacitor to apply the cardioverting electrical energy to the atria of the heart. The discharge control causes the applied cardioverting electrical energy to have a biphasic waveform having a first phase and a second phase of opposite polarity and equal time duration. The time durations of the first and second phases are each greater than four milliseconds, and the capacitance of the storage capacitor is greater than or equal to 120 $\mu$F.

7 Claims, 2 Drawing Sheets

IMPLANTABLE ATRIAL DEFIBRILLATOR PROVIDING REDUCED CARDIOVERSION DISCOMFORT

BACKGROUND OF THE INVENTION

The present invention generally relates to an automatic implantable atrial defibrillator for delivering cardioverting or defibrillating voltage to the atria of a patient and which is capable of providing effective cardioversion with reduced discomfort to the patient.

Atrial fibrillation is probably the most common cardiac arrhythmia. Although it is not usually a life threatening arrhythmia, it is associated with strokes thought to be caused by blood clots forming in areas of stagnate blood flow as a result of prolonged atrial fibrillation. Patients afflicted with atrial fibrillation generally experience palpitations of the heart and reduced cardiac output. This often leads to dizziness or, in extreme cases, to loss of consciousness.

Atrial fibrillation is often corrected by external defibrillation of the type well known in the art. This treatment involves applying a relatively large quantity of electrical energy to the heart with external skin surface electrodes. The energy is applied in synchronism with a detected R wave (electrical activation) of the heart. The treatment is very painful and can necessitate hospitalization for as many as a few days. Unfortunately, most often, it only provides temporary relief, lasting but a few weeks.

Drugs are available for reducing the incidents of atrial fibrillation. However, such drugs have many side effects. Also, many patients are resistant to them which greatly reduces their therapeutic effect.

In order to negate the need for external defibrillation and drug therapy, implantable atrial defibrillators have been proposed to provide relief for patients suffering from this cardiac arrhythmia. Two such defibrillators, although represented as being implantable, were not fully automatic, requiring human interaction for cardioverting or defibrillating the heart. Both of these defibrillators required the patient to recognize the symptoms of atrial fibrillation. One defibrillator required a visit to a physician for activating the defibrillator. The other defibrillator required the patient to activate the defibrillator with a magnet from external to the patient's skin.

It is preferable that an implantable cardiac device, such as an atrial defibrillator, be truly automatic. In order for an implantable atrial defibrillator to be truly automatic, it must be able to accurately detect atrial fibrillation and then safely apply cardioverting voltage to the atria to convert the same to normal sinus rhythm (NSR).

Detection of atrial fibrillation requires an atrial fibrillation detector to determine if sensed heart activity satisfies a fibrillation criteria. One such detector is fully disclosed in co-pending U.S. application Ser. No. 08/233,251, filed Apr. 26, 1994 in the names of Harley G. White and Joseph M. Bocek for SELECTIVE CARDIAC ACTIVITY ANALYSIS ATRIAL FIBRILLATION DETECTION SYSTEM AND METHOD AND ATRIAL DEFIBRILLATOR UTILIZING SAME. Another such detector is fully disclosed in co-pending U.S. application Ser. No. 08/278,055, filed Jul. 20, 1994 in the names of Jaeho Kim and Harley G. White for SYSTEM AND METHOD FOR REDUCING FALSE POSITIVES IN ATRIAL FIBRILLATION DETECTION. Both of the aforementioned co-pending applications are assigned to the assignee of the present invention and incorporated herein by reference. Each discloses a preferred embodiment wherein atrial cardiac events are detected from sensed atrial activity. Further, R waves are detected from sensed ventricular activity and atrial fibrillation is determined based upon atrial activity occurring between detected R waves.

If atrial fibrillation is detected, it is then necessary to apply cardioverting voltage to the atria to return the heart to NSR. To that end, a storage capacitor is charged to a voltage and then discharged to apply the cardioverting voltage to the heart. To assure that the cardioverting voltage is safely applied to the atria, it is preferred that the capacitor is discharged in synchronism with a detected R wave. To that end, co-pending U.S. application Ser. No. 08/259,476 filed Jun. 14, 1994 in the name of Harley G. White for CARDIOVERSION SYNCHRONIZATION SYSTEM AND METHOD FOR AN ATRIAL DEFIBRILLATOR, which is assigned to the assignee of the present invention and incorporated herein by reference discloses a synchronization system which includes two ventricular sense channels and requires that an R wave be sensed in both channels before the voltage may be applied. In addition, other synchronization criteria may be required.

In order to provide reasonable assurance that the cardioverting voltage will indeed successfully cardiovert the atria, the voltage from the storage capacitor should have a peak value above a determined minimum peak value for a given discharge duration to effectively cardiovert the atria. That voltage level is one measure commonly referred to as the defibrillation threshold.

Energy conservation in an implantable device is always a consideration. A study was conducted to determine what biphasic discharge duration resulted in the lowest required atrial cardioversion energy. The results of that study indicated that for a biphasic discharge, a total discharge duration of six milliseconds, with each phase having a three millisecond duration, rendered the lowest required cardioversion energy. Given this result, it was then determined that for a discharge period of six milliseconds, a storage capacitor having a capacitance of about 80 $\mu$F yielded the maximum energy transfer efficiency. Hence, the combination of a storage capacitor having a capacitance of about 80 $\mu$F and a total biphasic discharge time of about six milliseconds, from an energy utilization point of view, is the atrial cardioversion combination of choice. Storage capacitors having a capacitance of about 80 $\mu$F are also desirable because they can readily be made small enough to accommodate the size requirements for an implantable device.

Since patients suffering from atrial fibrillation will be conscious during cardioversion (unlike patients suffering from ventricular fibrillation), perceived discomfort or pain caused by the cardioversion is also an issue. Obviously, the less discomfort a patient experiences as a result of cardioversion the better. It has been determined that for many patients, an atrial defibrillation combination of a storage capacitance in the range of 80 $\mu$F and a total biphasic discharge time of six milliseconds is also, for most patients, a suitable choice in terms of cardioversion tolerance. However, some patients do experience discomfort with this combination of cardioversion conditions. The present invention is therefore directed to providing an atrial cardiovertor which will effectively cardiovert, but with reduced discomfort, those patients which experience discomfort when cardioverted with prior art cardiovertors. Additionally, the present invention provides for higher output energies when needed.

SUMMARY OF THE INVENTION

The present invention provides an implantable atrial cardiovertor for applying cardioverting electrical energy to atria of a heart. The cardiovertor includes a storage capacitor for storing electrical energy and a discharge control for controlling discharge of the storage capacitor to apply the cardioverting energy to the atria of the heart. The storage capacitor has a capacitance equal to or greater than 120 µF and the discharge control causes the storage capacitor to be discharged for a discharge time greater than eight milliseconds.

The present invention more particularly provides an implantable atrial cardiovertor for applying cardioverting electrical energy to atria of a heart, the cardiovertor including a storage capacitor having a capacitance and a discharge control for controlling discharge of the storage capacitor to apply the cardioverting electrical energy to the atria of the heart. The discharge control causes the applied cardioverting electrical energy to have a biphasic waveform having a first phase and a second phase of opposite polarity and equal time duration. The time durations of each of the first and second phases is six milliseconds. The capacitance of the storage capacitor is 160 µF.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
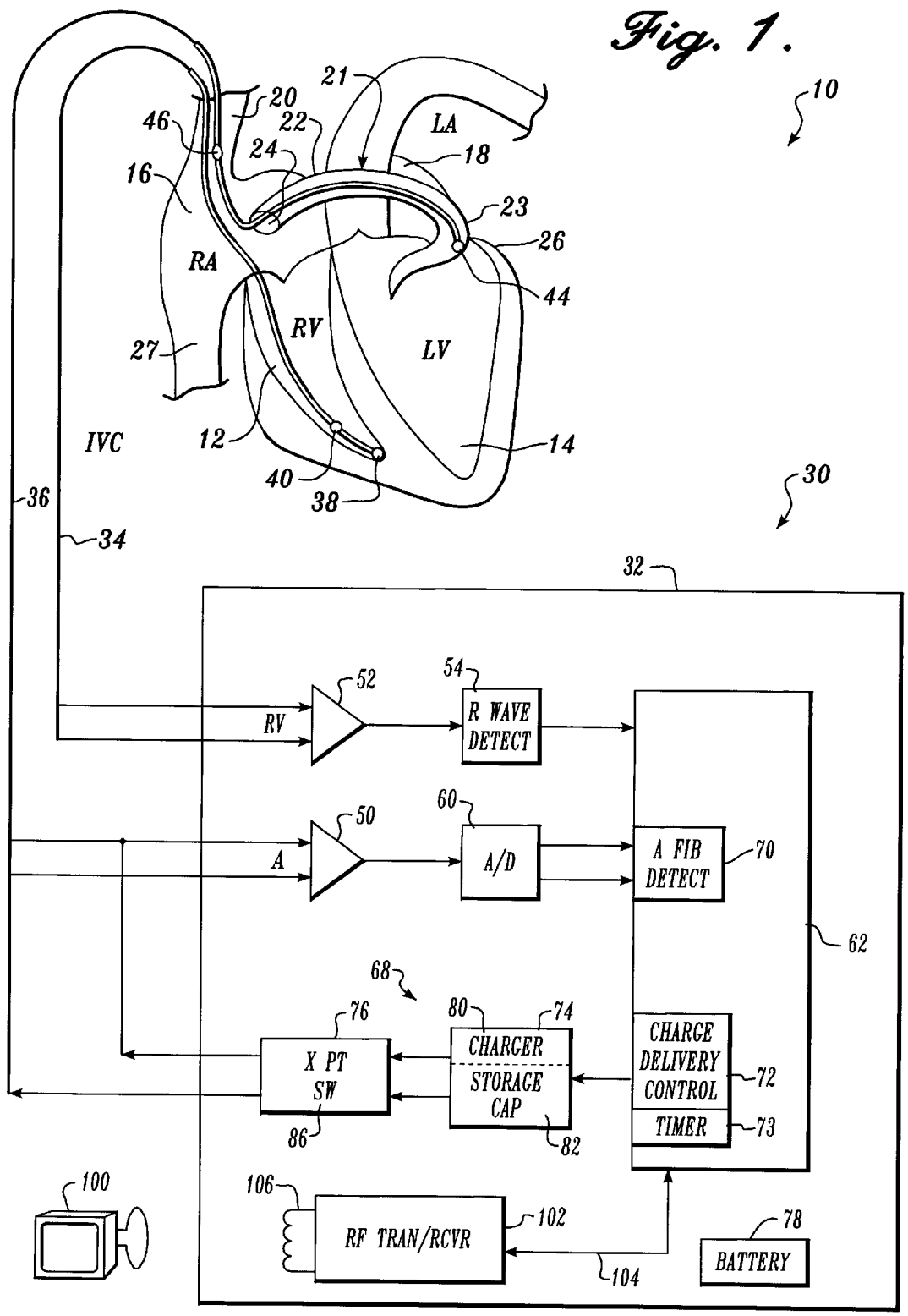
FIG. 1 is a schematic block diagram of a fully implantable atrial defibrillator embodying the present invention for applying defibrillating voltage to the atria of a human heart with reduced discomfort and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27. In addition, as used herein, the term "electrical activations" denotes R waves of the heart cardiac cycle which are depolarizations of the ventricles 12 and 14.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is preferably fed through the superior vena cava 20, into the right atrium 16, and then into the right ventricle 12.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16.

The first electrode 44 together with the second electrode 46 provide bi-polar sensing of heart activity in the atria 16 and 18. The first electrode 44 and the second electrode 46 further provide for the delivery of defibrillating electrical energy or voltage to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10.

Within the enclosure 32, the atrial defibrillator 30 includes a first sense amplifier 50, a second sense amplifier 52, and an R wave detector 54. The first sense amplifier 50 is coupled to the first electrode 44 and second electrode 46 of the second lead 36 for detecting atrial activity of the heart. The second sense amplifier 52 is coupled to electrodes 38 and 40 of lead 34 for detecting ventricular activity of the heart. The R wave detector 54 detects ventricular activations (R waves) from the detected ventricular activity.

The output of the first sense amplifier 50 is coupled to an analog to digital converter 60. The analog to digital converter 60 converts the analog signal representative of the sensed atrial activity of the heart to digital samples for further processing in a manner to be described hereinafter.

The enclosure 32 of the atrial defibrillator 30 further includes a microprocessor 62. The microprocessor 62 is preferably implemented in a manner as disclosed in the aforementioned copending U.S. application Ser. Nos. 08/233,251 and 08/278,055 to form an atrial fibrillation detector 70, a charge delivery and energy control stage 72, and a timer 73.

The microprocessor 62 is arranged to operate in conjunction with a memory (not shown) which may be coupled to the microprocessor 62 by a multiple-bit address bus (not shown) and a bi-directional multiple-bit database (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and conveys the date to the memory over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, such as defibrillation peak voltage levels into stage 72, or for receiving operating commands, the microprocessor 62 receives the programmable operating parameters and operating commands from an external controller 100 which is external to the skin of the patient and under the control of an operator, such as a physician. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters and operating commands from the external controller 100 which the receiver/transmitter 102 then conveys to the microprocessor 62 for storage in internal memory.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32 and for transmitting data to the external controller 100 from the implanted enclosure 32. One such communication system is disclosed, for example, in U.S. Pat. No. 5,342,408 which is also issued to the assignee of the present invention and incorporated herein by reference.

The charge delivery and energy control forms a part of a cardiovertor 68 which also includes a charger and storage capacitor circuit 74 and a discharge circuit 76. The charger and storage capacitor circuit 74 includes a charger 80 for charging a storage capacitor 82 with energy to a peak voltage. In accordance with the present invention, the storage capacitor 82 preferably has a capacitance greater than or equal to 120 $\mu$F. As will be illustrated hereinafter, the capacitance of capacitor 82 is preferably 160 $\mu$F. The discharge circuit 76 includes a crosspoint switch 86 for discharging the storage capacitor 82. The discharge circuit 76 is coupled to the first electrode 44 and the second electrode 46 of the second lead 36 for applying the cardioverting or defibrillating voltage to the atria when the capacitor 82 is discharged. Preferably, the discharge circuit 76 discharges the capacitor 82 so that the applied cardioverting energy has a biphasic waveform wherein the phases are of equal time duration and opposite polarity. The timer 73 controls the time duration of the biphasic waveform phases. U.S. Pat. No. 5,251,624 discloses cardioverting circuitry including charging and crosspoint switch circuitry which may be utilized in practicing the present invention.

Lastly, the defibrillator 30 includes a depletable power source 78, such as a lithium battery. It provides power to the electrical components of the atrial defibrillator 30.

When the atrial defibrillator 30 is operative in its normal operating mode, the atrial fibrillation detector 70, sense amplifier 50, and the analog to digital converter 60 are preferably enabled at predetermined times as disclosed in U.S. Pat. No. 5,464,432 issued on Nov. 7, 1995 for AN IMPLANTABLE ATRIAL DEFIBRILLATOR HAVING AN INTERMITTENTLY ACTIVATED FIBRILLATION DETECTOR, which patent is assigned to the assignee of the present invention and incorporated herein by reference. If the atrial fibrillation detector 70 determines that the atria 16 and 18 are in fibrillation and thus in need of cardioversion, the charge delivery control 72 causes the charger 80 to charge the storage capacitor 82 with energy to a peak voltage level above the patient's threshold. Then, when synchronization criteria are met as disclosed in the aforementioned U.S. application Ser. No. 08/259,476, for example, the charge delivery control 72 cause the discharge circuit 76 to discharge some of the voltage of capacitor 82 into electrodes 44 and 46 for cardioverting the atria.

In accordance with the present invention, the discharge pulse width or duration is longer than eight milliseconds and is preferably twelve milliseconds. This is made possible by a rather large capacitance value storage capacitor of greater than or equal to 120 $\mu$F and preferably 160 $\mu$F.

Discomfort or pain resulting from cardioversion is believed to be a nervous system response to the discharged voltage. The physiologic basis for this is that nerve tissue has a much faster membrane time constant than cardiac muscle. Therefore, shorter and higher peak voltage discharges create more pain or discomfort than do longer and lower peak voltage discharges. Hence, when a capacitance of, for example, 80 $\mu$F, is charged to the peak voltage necessary to satisfy the threshold for a 3 millisecond by 3 millisecond biphasic discharge waveform, it will cause more discomfort to be perceived when discharged than when a capacitor of, for example, 160 $\mu$F is discharged with a six millisecond by six millisecond biphasic waveform. Since the latter capacitor is to be discharged for a longer period, the peak voltage to which it must be charged to deliver adequate cardioverting energy will be less. Hence, two conditions work together to reduce perception of discomfort, lower peak discharge voltage and longer discharge time while the total energy delivered is equal.

Figure 2:
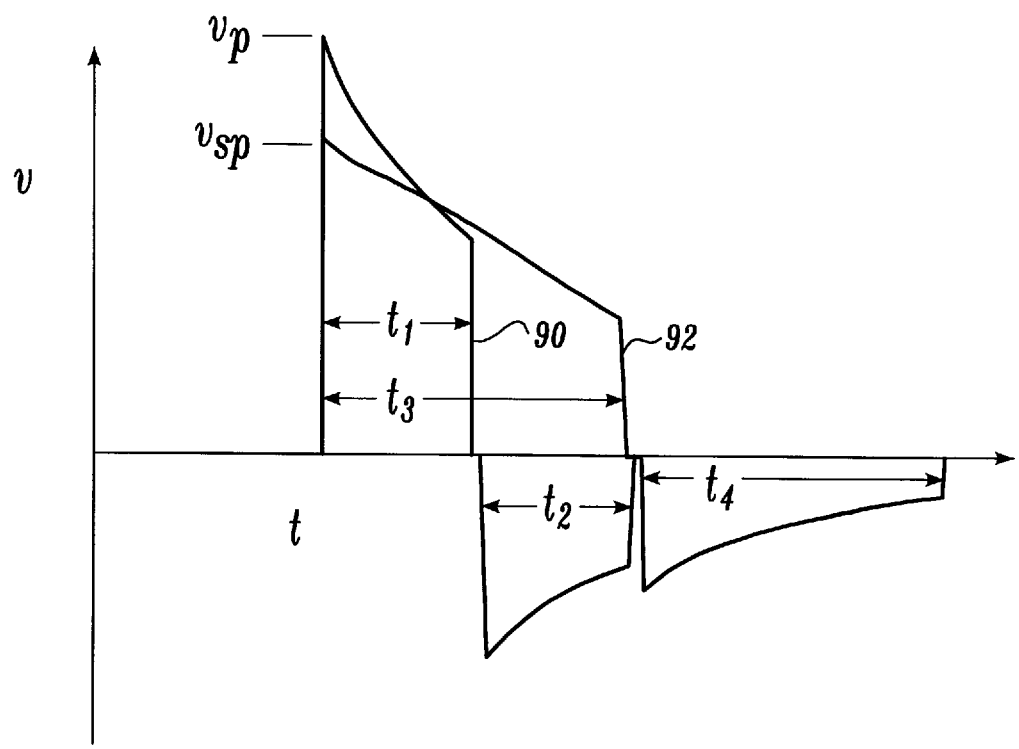
FIG. 2 illustrates superposed voltage versus time defibrillating voltage waveforms for illustrating principal aspects of the present invention.

FIG. 2 illustrates the differences in the two discharge voltage waveforms when using a storage capacitor of 80 $\mu$F and a storage capacitor of 160 $\mu$F. Waveform 90 is a three millisecond (3 ms) by three millisecond (3 ms) biphasic waveform produced using an 80 $\mu$F capacitor. Hence, both time periods or phases $t_1$ and $t_2$ are three milliseconds. The peak voltage Vp is the peak discharge voltage necessary to exceed the patient's threshold using an 80 $\mu$F capacitor and a 3 ms by 3 ms biphasic discharge waveform.

Waveform 92 is a six millisecond (6 ms) by six milliseconds (ms) biphasic waveform that results when using a 160 $\mu$F storage capacitor. The capacitor 82 is charged to a peak voltage of only Vsp. Vsp is less than Vp but sufficient to exceed the patient's defibrillation threshold, but not the patient's discomfort threshold when using a biphasic discharge waveform of 6 ms by 6 ms. As a result, the time periods or phases $t_3$ and $t_4$ are six milliseconds and made possible because the capacitor is 160 $\mu$F and hence discharged more slowly than the 80 $\mu$F capacitor.

While a particular embodiment of the present invention has been shown and described herein, modifications may be made. For example, the principles of the present invention also apply to monophasic discharge waveforms. Hence, it is therefore intended to cover in the appended claims, all such changes and modifications which fall within the true spirit and scope of the invention.

What is claimed is:

1. An implantable atrial cardioverter for applying cardioverting electrical energy to atria of a heart, said cardioverter including at least one lead having an electrode adapted to be in electrical contact with an atrium of the heart, a storage capacitor for storing electrical energy and a discharge control for controlling discharge of the storage capacitor to apply the cardioverting energy to the electrode adapted to be in electrical contact with the atrium of the heart, said storage capacitor having a capacitance greater than or equal to 120 $\mu$F and said discharge control causing said storage capacitor to be discharged for a discharge time greater than eight milliseconds.

2. A cardiovertor as defined in claim 1 wherein the storage capacitor has a capacitance of 160 $\mu$F.

3. A cardiovertor as defined in claim 1 wherein said discharge control causes said storage capacitor to be discharged for a discharge time of twelve milliseconds.

4. A cardiovertor as defined in claim 1 wherein said discharge control controls the discharge of the storage capacitor such that the applied cardioverting electrical energy has a biphasic waveform.

5. A cardiovertor as defined in claim 4 wherein a first phase and a second phase of the biphasic waveform have equal time durations.

6. A cardiovertor as defined in claim 5 wherein each of the first and second phases has a time duration of six milliseconds.

7. An implantable atrial cardioverter for applying cadioverting electrical energy to atria of a heart, said cardioverter including at least one lead having an electrode adapted to be in electrical contact with an atrium of the heart, a storage capacitor having a capacitance and a discharge control for controlling discharge of the storage capacitor to apply the cardioverting electrical energy to the electrode adapted to be in electrical contact with the atrium of the heart, said discharge control including means for causing the applied cardioverting electrical energy to have a biphasic waveform, said biphasic waveform having a first phase having a polarity and a second phase having a polarity, wherein the polarity of the first phase is opposite the polarity of the second phase, wherein each said first and second phases has a time duration, wherein the time durations of the first and second phases are equal, and wherein the time durations of each of the first and second phases is six milliseconds, and said capacitance of said storage capacitor being 160 $\mu$F.

* * * * *